United States Patent

Naqui

[11] Patent Number: 5,166,054
[45] Date of Patent: Nov. 24, 1992

[54] METHOD FOR IMMUNOASSAY USING LACTOPEROXIDASE, STARCH AND IODINE

[75] Inventor: Ali Naqui, Sparks, Md.

[73] Assignee: Becton, Dickinson and Company, Franklin Lakes, N.J.

[21] Appl. No.: 636,800

[22] Filed: Jan. 2, 1991

[51] Int. Cl.$^5$ ............... C12Q 1/28; G01N 33/535
[52] U.S. Cl. ................. 435/7.91; 435/7.9; 435/7.92; 435/28
[58] Field of Search .......... 435/7.91, 7.92, 975, 435/28, 7.9; 436/518, 530, 808

[56] References Cited

U.S. PATENT DOCUMENTS

| Re. 28,575 | 10/1975 | Bauer | 435/28 |
| 2,981,606 | 4/1961 | Keston et al. | 23/230 |
| 3,802,842 | 4/1974 | Lange et al. | 23/253 TP |
| 3,886,045 | 5/1975 | Meiattini | 435/28 |
| 4,016,043 | 4/1977 | Schuurs et al. | 195/103.5 R |
| 4,446,232 | 5/1984 | Liotta | 435/7 |
| 4,504,579 | 3/1985 | Sun | 435/28 |
| 4,687,734 | 8/1987 | Chester | 435/7 |
| 4,740,468 | 4/1988 | Weng et al. | 435/7 |

Primary Examiner—Sam Rosen
Attorney, Agent, or Firm—Richard E. Brown; Donna R. Fugit

[57] ABSTRACT

A method for immoassay includes a membrane coated with a capture antibody and starch. A solution suspected of containing an antigen is passed through the membrane. Antigen binds to the capture antibody. A conjugate of a detection antibody and lactoperoxidase is passed through the membrane to form a sandwich on the membrane. A substrate composition including peroxide and iodide is passed through. The lactoperoxidase catalyzes oxidation of iodide by the peroxide to give iodine which reacts with the starch to give a blue color. The invention includes a kit of materials for performing the assay of the invention.

18 Claims, No Drawings

METHOD FOR IMMUNOASSAY USING LACTOPEROXIDASE, STARCH AND IODINE

BACKGROUND OF THE INVENTION

1. Field of the Invention

This invention relates to immunoassay of an analyte and materials relates to immunoasay of an analyte and materials used therein, and more particularly relates to a method and materials for enzyme immunoassay in which the analyte is detected by a colored spot on a solid support.

2. Background of the Invention

Assay systems which are both rapid and sensitive have been developed to determine the concentration of a substance in a antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous, requiring a separation of bound tracer from free (unbound) tracer or homogeneous in which a separation step is not required.

Enzymes have often been used as labels in immunoassay. In conventional enzyme immunoassay (EIA), an enzyme is covalently conjugated with one component of a specifically binding antigen antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

Peroxidases are commonly used as labels in EIA. These enzymes catalyze the oxidation of a substrate to a product by hydrogen peroxide. Horseradish peroxidase (HRP) is a widely used example of this class of enzymes. U.S. Pat. No. 4,016,043 to Schuurs et al. discloses EIA using HRP.

Numerous substrates oxidized by hydrogen peroxide under catalysis by a peroxidase are known. Among the more common are 3,3'-diaminobenzidine (DAB), 5-amino salicylic acid, o-dianisidine, o-toluidine and, most commonly, o-phenylenediamine (OPD).

These known peroxidase substrates, while useful, have certain limitations. For example, the oxidation product of OPD has sufficient water solubility so that it gives an excellent visual readout in a solution assay. On the other hand, the water solubility of the oxidation product causes rapid diffusion when the product is deposited as a spot on a solid phase, such as a membrane or dipstick. This severely reduces assay sensitivity and limits usefulness of OPD in ELISA procedures.

Several peroxidase substrates which generate insoluble products are known, such as DAB, 3-amino-9-ethylcarbazole, 3,3',5,5'-tetramethyl-benzidine, and 4-chloro-1 naphthol. While effective, these substrates do not generate as much color as is developed with OPD and peroxidase.

Lactoperoxidase (LPO) is a commercially available enzyme from milk which catalyzes the oxidation of iodide to iodine by peroxide. This reaction has been used for preparation of an immunoassay reagent labeled with $^{127}$I in U.S. Pat. No. 4,687,734 to Chester.

U S. Pat. No. 4,504,579 to Sun discloses an antibiotic-stabilized conjugate of LPO and an immunological binding component useful as an EIA reagent.

There is need for a method for peroxidase based EIA which gives a stable, well defined and deeply colored spot on a membrane or dipstick. It is toward fulfillment of this need that this application is directed.

SUMMARY OF THE INVENTION

A method for immunoassay of an analyte takes advantage of the blue color which develops on reaction of starch and iodine. A solid support coated with a capture antianalyte is contacted with the analyte and a detection antianalyte conjugated to LPO. A substrate having iodide and a source of peroxide is contacted with the support. The LPO catalyzes oxidation of the iodide by the peroxide to give iodine which reacts with starch to give a blue color indicative of analyte.

In a preferred embodiment of the invention, the support is a porous membrane and the assay is performed by flow-through assay. In the most preferred embodiment, the starch is absorbed onto the membrane.

The invention includes a kit of materials for performing the assay.

Thus, the invention provides a method for immunoassay in which LPO is the label and the signal is an instantaneously formed, permanent, colored spot on a solid support. No color development period is needed, and since the color does not change with time, no stop solution is necessary, as required by most colorimetric EIAs. Further, LPO is a particularly attractive enzyme label because body fluids and tissues which are generally the source of the analyte have very little endogenous LPO activity. In contrast, in assays using conventional enzymes such as alkaline phosphatase as the label, endogenous enzyme activity is often the cause of false positives.

The high sensitivity of the assay using LPO on a membrane makes possible a simple assay device providing visual rather than instrumental readout. The simplicity of the assay of the invention makes it particularly well suited for use in a physician's office or even in the home.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

One aspect of the present invention is a method for EIA in which LPO serves as the enzyme label and the blue color resulting from reaction of starch and iodine is the assay signal.

In general, the immunoassay of the invention may be used to determine an antigen, an antibody or a hapten. In this disclosure, the substance to be determined is referred to as the analyte. Preferred assays include an antianalyte which binds substantially specifically to the analyte. Thus, if the analyte is an antigen, a suitable antianalyte would be a specific antibody. If the analyte is a hapten, a suitable antianalyte would be an antihapten antibody. If the analyte is an antibody, a suitable antianalyte would be a specific anti antibody. Antibodies useful in the invention as antianalytes may be either monoclonal or polyclonal. Raising of specifically binding antibodies is well known in the art and no further description of this aspect of the invention is needed for a full understanding of the invention.

Preferred analytes are antigens, most preferably viral antigens present in a body fluid, such as Adenovirus, Parainfluenza 3 virus, Herpes simplex virus (HSV), Respiratory syncytial virus (RSV), and Influenza A (Flu A). The invention will hereinafter be described generically in terms of an antigen analyte.

The antigen may be from any source, such as a body fluid, a culture of microorganisms or a cellular extract thereof. Preferably, the antigen may be assayed in a liquid sample, such as the body fluid, or it may be isolated from the body fluid and subsequently introduced into a different liquid, such as buffer.

The assay of the invention may be performed by any conventional solid phase technique in which the presence or absence of an analyte in a sample is detected by LPO catalyzed conversion of a substrate to a colored product. For example, the assay of the invention may be performed by immunochromatography. In this procedure, a liquid phase containing antigen to be detected migrates by capillary action across a solid support, such as a glass plate, having various assay components deposited on adjacent but separated zones thereof. Representative of this procedure is the assay disclosed in U.S. Pat. No. 4,446,232 to Liotta.

Another suitable assay technique uses a dipstick. In this procedure, the solid support, usually a glass plate having a binder containing a capture antibody thereon, is dipped alternately into the test liquid, liquids containing assay reagents and wash liquids. In the last dip, an enzyme captured on the dipstick in proportion to the concentration of antigen in the test liquid converts a substrate for the enzyme to a colored product which deposits on the dipstick and which is indicative of the presence of antigen.

Other suitable solid supports well known in the immunoassay art are the well of a microtiter plate and the inside wall of a tube or cuvette. Such supports may be of glass or a polymer, such as polystyrene, polyvinyl, polyolefin or polyurethane.

A preferred assay technique is flow-through assay in which the solid support is a porous membrane. The membrane may be positioned in any suitable assay device adapted for flow through assay as known in the art. In preferred devices, flow of assay liquids is promoted by capillary action induced by a pad of absorbent material adjacent the membrane, and the membrane and absorbent pad are mounted in a suitable housing. Membrane flow through assay and various devices therefor have been disclosed and several devices are commercially available. The invention will hereinafter be described generically in terms of the preferred membrane assay.

The porous membrane may be of any material which does not interfere in any way with any other component or step of the assay. Suitable membranes are, for example, of glass fiber, polyvinylidene difluoride, polycarbonate, nitrocellulose and nylon. Such membranes are well-known in the art and many are commercially available from suppliers such as Pall (East Hills, N.Y.), Millipore (Bedford, Mass.) and Schleicher and Schuell (Keene, N.H.).

The membrane may be coated with starch and an antianalyte. In the preferred assay where the analyte is an antigen, the antianalyte may be an antibody which binds specifically to the antigen and thereby hereinafter referred to as the capture antibody. If the analyte is an antibody, the capture antianalyte may be a specifically binding antigen. If the analyte is a hapten, it may be necessary to conjugate the hapten to a protein in order to raise a suitable well known in the art of hapten immunoassay, and further details with respect to this aspect of the invention are not needed for a complete understanding of the invention.

The coating of starch may be applied to the membrane either prior to, concurrently with or subsequent to the capture antibody. Coating may be by any procedure as known in the art. A suspension or preferably a solution, most preferably an aqueous solution, of the capture antibody and starch is merely passed through the membrane. The antibody and starch are physically absorbed into the polymeric matrix of the membrane and do not wash off during any subsequent passage of reagents or wash solutions.

In some cases, it may be advantageous to further coat the membrane with an inert protein to fill any binding sites on the membrane not occupied by the capture antibody or the starch. (In the present disclosure, the term inert protein means a protein which is immunologically unreactive toward any other component of the assay and which does not substantially bind nonspecifically to other proteins in the assay medium, with the understanding that the inert protein may well be immunologically reactive toward other materials which are not part of the assay of the invention.) Representative nonlimiting examples of suitable inert proteins are casein and albumin, although others will be evident to those skilled in the art. As is well known in the art, the inert protein serves to avoid or reduce nonspecific binding of other proteins.

The membrane coated with capture antibody and starch may be contacted with the sample suspected of containing the antigen in order to bind the antigen to the antibody. Preferably, the sample is applied to the coated membrane and allowed to pass through the membrane in a transient, flow through format for about 1 to 15, preferably about 5 minutes at a temperature of about 0° to 50° C., preferably about ambient temperature. By this procedure, antigen in the sample is captured on the membrane in proportion to its concentration in the sample.

A tracer including a second antianalyte (hereinafter referred to as the detection antibody) having LPO conjugated thereto may then be passed through the membrane. Antibody enzyme conjugates are conventional in the art and may be prepared by a variety of well known synthetic procedures. No further details with respect to preparation of the LPO conjugate are needed for a full understanding of the invention.

When the LPO detection antibody conjugate passes through the membrane, the antibody portion binds to antigen captured on the membrane to give an antibody:antigen:antibody sandwich on the membrane, hereinafter referred to as the bound fraction. Alternatively, the antigen and detection antibody may be mixed and passed through the coated membrane together to form the bound fraction.

After binding of the tracer to antigen on the membrane, a substrate for the LPO may be added. The substrate may include peroxide and iodide ion. The peroxide may be in the form of an alkali metal salt capable of releasing peroxide, much as sodium perborate or preferably may be hydrogen peroxide. The iodide may be hydrogen iodide or preferably be in the form of an alkali metal iodide. The peroxide may be enzymaticaly generated in situ by passing a solution of glucose and glucose oxidase through the membrane wherein the glucose is oxidized by oxygen in the air under catalysis by the glucose oxidase to hydrogen peroxide.

When the solution of peroxide and iodide is passed through the membrane, LPO on the membrane catalyzes the oxidation of the iodide by the peroxide to iodine. The iodine reacts with the starch on the membrane to give an instantaneous deep blue color which is indicative of antigen in the test sample. If no antigen is present, no blue color appears because no LPO was affixed to the membrane. The color does not wash off and does not change with time.

In an alternative embodiment of the invention, the starch may be supplied as part of a substrate composition instead of being coated on the membrane. Thus, a solution or suspension containing starch, iodide and peroxide may be passed through the membrane having a bound fraction thereon. The same sequence of reactions as described above takes place to give a blue color indicating the presence of antigen in the test liquid. If antigen is absent, no bound fraction forms on the membrane and no blue color forms.

The invention includes a reagent kit or package of materials for performing the assay of the invention. The kit may include a solid support, preferably a membrane coated with starch and a capture antianalyte and optionally coated with an inert protein. Another component of the kit may be a detection antianalyte conjugated to LPO. Various reagents to serve as components of a substrate system for LPO, such as iodide, peroxide, glucose and glucose oxidase may be included. These reagents may be included individually in the kit or they may be supplied in various combinations either as solutions in an appropriate vehicle such as water or buffer, or in a dehydrated or lyophilized form for reconstitution with water or buffer before use. The kit may also include reference standards for the analyte as, for example, one or more analyte samples of known concentration, or it may include other reagents, substrates, or solutions, such as saline or buffers and utensils such as vials or droppers useful in carrying out the assay. The membrane may be provided in a housing, preferably plastic, containing a material positioned under the membrane, such as absorbent paper, to facilitate flow of assay liquids through the membranes by capillary action.

The following examples are provided to further describe the invention but are not to be considered in any way as limitative of the invention.

EXAMPLE I

Detection of Lactoperoxidase on a Membrane

I. Materials

A. Lactoperoxidase (LPO) Sigma L- 8257 Lot 107F-3853; 49F- 3845

B. Horseradish Peroxidase (HRP)—Sigma P—6782 Lot 69F—9525

C. Soluble Starch—Sigma S 9765 Lot 78F- 0919; 109F- 0288

D. Potassium Iodide (KI)—Sigma P- 8256 Lot 49F-0727

E. Hydrogen Peroxide ($H_2O_2$)—Sigma H-1009 Lot 119F- 3485

F. Assay Device

Top Layer—Five micron pore size nitrocellulose membrane (MSI, Westoro, Mass.) or 0.45 micron pore size nitrocellulose membrane (Schleicher & Schuell, Keene, N.H.)

Next Layer—Non woven rayon sheet (Schleicher & Schuell, Keene, N.H.)

Bottom Layer—Cellulose absorbent pads (2) (Filtration Sciences, Mount Spring, Pa.)

These layers were encased in a plastic holder which included a receiving well formed above the top layer. All reagents were added through the receiving well.

II. Procedure

The nitrocellulose membrane was soaked in 1% solution of soluble starch for 5 minutes and allowed to dry in air. the starch-treated nitrocellulose was encased in the assay device. Various concentrations of LPO (in 50 mM phosphate buffer, pH 7.2) were added to the membrane through a "sample focuser" in a triangular shape. After the LPO was absorbed, the sample focuser was removed, and a substrate solution ($\sim 10$ mM KI+ $\sim 1$ mM $H_2O_2$) in 50 mM phosphate buffer, pH 7.2, was added and the color generation was detected. The following results were obtained:

| Conc. of LPO ($\mu$g/ml) | Color |
| --- | --- |
| 1 | blue-black |
| 0.1 | blue |
| 0.01 | faint blue |
| 0.001 | — |

EXAMPLE II

Procedure for LPO based Immunoassay

The membrane of Example I is coated with a capture antibody specific for an antigen to be detected, then coated with starch as described in Example I. The membrane and filter stack are assembled in the assay device of Example I. A test liquid suspected of containing an antiqen is passed through the membrane. The membrane is washed with a suitable wash liquid. A solution containing a conjugate of lactoperoxidase with a detection antibody specific for the antigen is passed through the membrane followed by wash liquid. A solution containing iodide ion and hydrogen peroxide is passed through the membrane. An instantaneous formation of a blue color on the membrane indicates that antigen is present in the test liquid.

EXAMPLE III

Comparison of LPO with HRP

A. In solution:

A peroxide substrate solution (10 mM KI+mM $H_2O_2$) was added to each of 3 cuvettes. Cuvette 1 received HRP at a concentration of $6.3 \times 10^{-10}$M. Cuvette 2 received $3.2 \times$M LPO. Cuvette 3 received no enzyme as a control.

The reaction was monitored at 350 nm in a spectrophotometer (detection of $I_2$ formation). The absorbance did not change where HRP or no enzyme was added. The cuvette with half the amount of LPO turned yellow and the absorbance increased rapidly before plateauing. This experiment shows that HRp does not catalyze the oxidation of KI by $H_2O_2$ under the conditions of the experiment, whereas LPO does.

B. On solid phase:

The procedure of Example I was repeated using HRP as the enzyme. No blue spot was seen on the membrane.

C. Conclusion:

These two experiments clearly demonstrate that the conditions of the experiment, LPO catalyzes the reactions between KI, $H_2O_2$ and starch producing an intense blue color, whereas HRP, does not.

What is claimed is:

1. A method for detecting an analyte in a liquid comprising:
  a) bringing a solid support coated with starch and a first antianalyte into contact with a liquid suspected of containing an analyte and a tracer including lactoperoxidase conjugated to a second antianalyte whereby a bound fraction which includes said tracer is formed on said support;
  b) contacting said support with iodide and a source of peroxide whereby lactoperoxidase on said support catalyzes oxidation of said iodide to iodine; and
  c) determining that said analyte is present in said liquid by a blue color on said support due to reaction of said iodine with said starch.

2. The method of claim 1 wherein said first antianalyte is selected from the group consisting of an antigen and an antibody.

3. The method of claim 1 wherein said analyte is selected from the group consisting of an antigen, an antibody and a hapten.

4. The method of claim 1 wherein said iodide is selected from the group consisting of hydrogen iodide and an alkali metal iodide.

5. The method of claim 1 wherein said source of peroxide is selected from the group consisting of hydrogen peroxide and an alkali metal perborate.

6. The method of claim 1 wherein said peroxide is generated in situ from a mixture of glucose and glucose oxidase.

7. A method for detecting an analyte in a liquid comprising:
  a) bringing a solid support coated with an antianalyte into contact with a liquid suspected of containing an analyte and a tracer including lactoperoxidase conjugated to a second antianalyte whereby a bound fraction which includes said tracer is formed on said support;
  b) contacting said support with iodide, starch and a source of peroxide whereby lactoperosidase on said support catalyzes oxidation of said iodide by said peroxide to give iodine; and
  c) observing said support for a blue color due to reaction of said iodine with said starch, the presence of said blue color indicating that the liquid contains analyte.

8. A method for detecting an antigen in a liquid comprising:
  a) passing a first liquid suspected of containing an antigen through a porous membrane coated with starch and a first antibody whereby said antigen binds to said first antibody;
  b) passing a second liquid containing a second antibody conjugated to lactoperoxidase through said membrane whereby said second antibody binds to said antigen to give a bound fraction including said lactoperoxidase on said membrane;
  c) passing a third liquid containing peroxide and iodide through said membrane whereby lactoperoxidase on said membrane catalyzes oxidation of said iodide by said peroxide to give iodine, said iodine reacting with said starch to give a blue color on said membrane; and
  d) detecting said antigen in said first liquid by said blue color.

9. A kit of materials for performing an assay for an analyte comprising a solid support coated with a capture antianalyte, a tracer including lactoperoxidase conjugated to a detection antianalyte, starch, iodide and a source of peroxide.

10. The kit of claim 1 wherein said starch is coated on said support.

11. The kit of claim 9 wherein the source of peroxide is peroxide.

12. The kit of claim 9 wherein the source of peroxide is glucose and glucose oxidase.

13. The kit of claim 9 further comprising a known quantity of said analyte to serve as a reference standard.

14. The kit of claim 9 wherein at least one of the assay reagents is supplied in dehydrated form.

15. The kit of claim 14 further comprising a reconstitution liquid.

16. A kit of materials for performing an assay for an antigen comprising:
  a) an enclosure;
  b) a filter stack in said enclosure, said filter stack including a porous membrane coated with starch and a capture antibody and a pad of absorbent material in contact with said membrane;
  c) a tracer including lactoperoxidase conjugated to a detection antibody; and
  d) a substrate for said lactoperoxidase comprising iodide.

17. The kit of claim wherein said substrate further comprises peroxide.

18. The kit of claim 16 further comprising lucose and glucose oxidase.

* * * * *